US006638284B1

(12) United States Patent
Rousseau et al.

(10) Patent No.: US 6,638,284 B1
(45) Date of Patent: Oct. 28, 2003

(54) KNITTED SURGICAL MESH

(75) Inventors: Robert A. Rousseau, Ottsville, PA (US); Robert Dougherty, Reading, PA (US)

(73) Assignee: Ethicon, Inc., Somerville, NJ (US)

( * ) Notice: Subject to any disclaimer, the term of this patent is extended or adjusted under 35 U.S.C. 154(b) by 28 days.

(21) Appl. No.: 09/723,854

(22) Filed: Nov. 28, 2000

Related U.S. Application Data

(63) Continuation-in-part of application No. 09/328,061, filed on Jun. 8, 1999, now abandoned.

(51) Int. Cl.$^7$ ................................................ A61F 2/00
(52) U.S. Cl. ..................... 606/151; 606/213; 66/193; 66/195
(58) Field of Search .................. 66/195, 193; 606/151, 606/213

(56) References Cited

U.S. PATENT DOCUMENTS

| | | | | |
|---|---|---|---|---|
| 2,671,444 A | * | 3/1954 | Pease, Jr. ..................... 606/151 |
| 3,054,406 A | * | 9/1962 | Usher ..................... 139/426 R |
| 3,124,136 A | * | 3/1964 | Usher ......................... 606/213 |
| 4,193,137 A | * | 3/1980 | Heck ......................... 623/1.52 |
| 4,347,847 A | * | 9/1982 | Usher ......................... 128/898 |
| 4,452,245 A | * | 6/1984 | Usher ......................... 606/151 |
| 4,520,821 A | * | 6/1985 | Schmidt et al. ............. 435/399 |
| 4,557,264 A | * | 12/1985 | Hinsch ....................... 428/364 |
| 4,633,873 A | * | 1/1987 | Dumican et al. ........... 606/151 |
| 4,652,264 A | * | 3/1987 | Dumican .................... 623/1.38 |
| 4,655,221 A | * | 4/1987 | Devereux .................... 606/151 |
| 4,769,038 A | * | 9/1988 | Bendavid et al. ........... 606/151 |
| 4,838,884 A | * | 6/1989 | Dumican et al. ........... 604/364 |
| 4,911,165 A | * | 3/1990 | Lennard et al. .......... 264/210.8 |
| 5,002,551 A | * | 3/1991 | Linsky et al. ............... 606/151 |
| 5,292,328 A | * | 3/1994 | Hain et al. .................. 264/103 |
| 5,540,982 A | * | 7/1996 | Scholz et al. ................ 26/18.6 |
| 5,569,273 A | | 10/1996 | Titone et al. |
| 5,771,716 A | * | 6/1998 | Schlussel ..................... 66/193 |
| 6,443,964 B1 | | 9/2002 | Ory |

FOREIGN PATENT DOCUMENTS

| | | |
|---|---|---|
| EP | 0 334 046 | 6/1997 |
| FR | 2 766 698 A | 2/1999 |
| WO | WO 98 14134 A | 4/1998 |
| WO | WO 98/37813 | 9/1998 |

OTHER PUBLICATIONS

Ory, Francois R, et al; "Three–dimensional open–worked prosthetic fabric"; Sep. 3, 2002; Abstract of French Patent FR 2 766 698 A; esp@cenet database–12.
European Search Report EP00304819 dated Aug. 22, 2002.

* cited by examiner

*Primary Examiner*—Amy Vanatta
*Assistant Examiner*—Robert H. Muromoto, Jr

(57) ABSTRACT

A knitted surgical mesh formed from a yarn. The knitted mesh has from about 40 to about 80 courses per inch and from about 7 to 11 wales per inch, and a pore size percentage greater than 50%.

16 Claims, 3 Drawing Sheets

|← 1mm →|

KNITTED SURGICAL MESH

This is a Continuation-in-part of prior application Ser. No. 09/328,061, filed Jun. 8, 1999 now abandoned.

FIELD OF THE INVENTION

This invention relates to a textile material and, in particular, to a surgical mesh of knit construction fabricated from a polypropylene monofilament yarn.

BACKGROUND

Hernia repairs are among the more common surgical operations which may employ mesh fabric prosthesis. Such mesh fabric prostheses are also used in other surgical procedures including the repair of anatomical defects of the abdominal wall, diaphragm, and chest wall, correction of defects in the genitourinary system, and repair of traumatically damaged organs such as the spleen, liver or kidney.

Mesh fabrics for use in connection with hernia repairs are disclosed in U.S. Pat. Nos. 5,292,328, 4,769,038 and 2,671,444. Knitted and woven fabrics constructed from a variety of synthetic fibers and the use of the fabrics, in surgical repair are also discussed in U.S. Pat. Nos. 3,054,406; 3,124,136; 4,193,137; 4,347,847; 4,452,245; 4,520,821; 4,633,873; 4,652,264; 4,655,221; 4,838,884;. 5,002,551; and European Patent Application No. 334,046.

The examples of mesh that have been cited are focused on overcoming basic procedural needs regardless of foreign body effects on the patient. One example is Marlex mesh, which is a very dense knitted fabric structure with low porosity. The mesh, when utilized in some types of herniaplasty such as giant prosthetic reinforcement of the visceral sac (GPRVS), is considered too stiff and lacks the ability to conform to the natural shape of the patients anatomy. Further, the mass of polypropylene fiber per unit area is excessive relative to the strength provided by the reinforcement mesh.

The mesh disclosed in U.S. Pat. No. 5,292,328 (Hain et al.) is intended to be supple enough for GPRVS procedures and is manufactured out of a fine denier multi-filament polypropylene that has been stiffened. While the mesh is stronger than its multi-filament polyester procedural alternative, it relies upon a multi-filament construction and is stiffer than the polyester counterpart. Additionally, the use of a multi-filament textile in the presence of an infection is not desirable. It is generally believed that the small interstices between the fine filaments are able to harbor an infection and prevent proper healing of the wound. Further, the increase surface area due to the fine denier filaments causes the mesh structure to become extremely opaque or reflective to endoscopic camera lighting.

With the advent of endoscopic hernia repair, a need to produce meshes that are less reflective of the high intensity lighting, utilized to perform the surgery, and enables visualization of repair sight through the mesh itself is necessary. U.S. Pat. No. 5,569,273 (Titone) discloses a dual bar warp knitted structure that attempts to increase the pore size of the mesh and reduce the reflective surfaces of the knitted structure. While this construction increases the pore size of the mesh, it degrades the strength of the knitted structure. Further, the knitted structure results in a fabric that is too stiff for GPRVS procedures and increases total fabric density. Additionally, the open individual cells do not enable fixation near the edge of the knitted mesh structure after cutting.

In all of the examples cited, the meshes are provided, and intended, as the long-term primary structural support for the abdominal wall repair. From a patient need perspective, the growth of scar tissue on the mesh provides a large portion of the final structural integrity of the implanted prosthesis. The mesh is simply a scaffold upon which the scar tissue may form. This is apparent given the fact that as the natural scar tissue contracts during healing, the mesh effectively becomes embedded within the scar itself and is no longer flat and is therefore unable to exert tensile reactive forces. Therefore, the initial mesh burst strength is only relevant prior to scar tissue formation and does not need to exceed the forces capable of being held by the points of fixation. In the presence of the scar tissue, all of the examples cited are excessive relative to the clinical need of the patient and simply add to the mass of foreign matter residing in the body after natural healing has occurred It is desirable for surgical mesh fabric prosthesis to exhibit certain properties and characteristics. In particular, the mesh should have a burst strength sufficient to ensure that the mesh does not break or tear after insertion into a patient. The mesh should also have a pore size that enables easy visualization of structures through the mesh, minimize camera light reflection and provide a density of crossing fibers sufficient to facilitate fastening in an endoscopic environment. In addition, the construction of the mesh should provide the maximum burst resistance while minimizing foreign body mass and enhancing fabric pliability.

It is an object of the present invention to provide a knitted surgical mesh having a high burst strength/fabric weight ratio, possessing a large pore size (with a density of crossing fibers to enable easy fastening), which has a greater flexibility than known knitted surgical mesh fabrics while minimizing foreign body mass in the clinical environment.

These and other objects and advantages of the invention will become more fully apparent from the description and claims, which follow or may be learned by the practice of the invention.

SUMMARY OF THE INVENTION

The present invention is directed to a knitted surgical mesh formed from a yarn. The knitted mesh has from 40 to 80 courses per inch and from 7 to 11 wales per inch, a flexibility of from about 80 to about 250 mg-cm, a burst strength greater than 105 pounds per square inch and an average porosity of greater than 50%.

BRIEF DESCRIPTION OF THE DRAWINGS

In order that the manner in which the above-recited and other advantages and objects of the invention are obtained and can be appreciated, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode thereof will be described and explained with additional specificity and detail through the use of the accompanying drawings.

DESCRIPTION OF THE PREFERRED EMBODIMENTS

Figure 1:
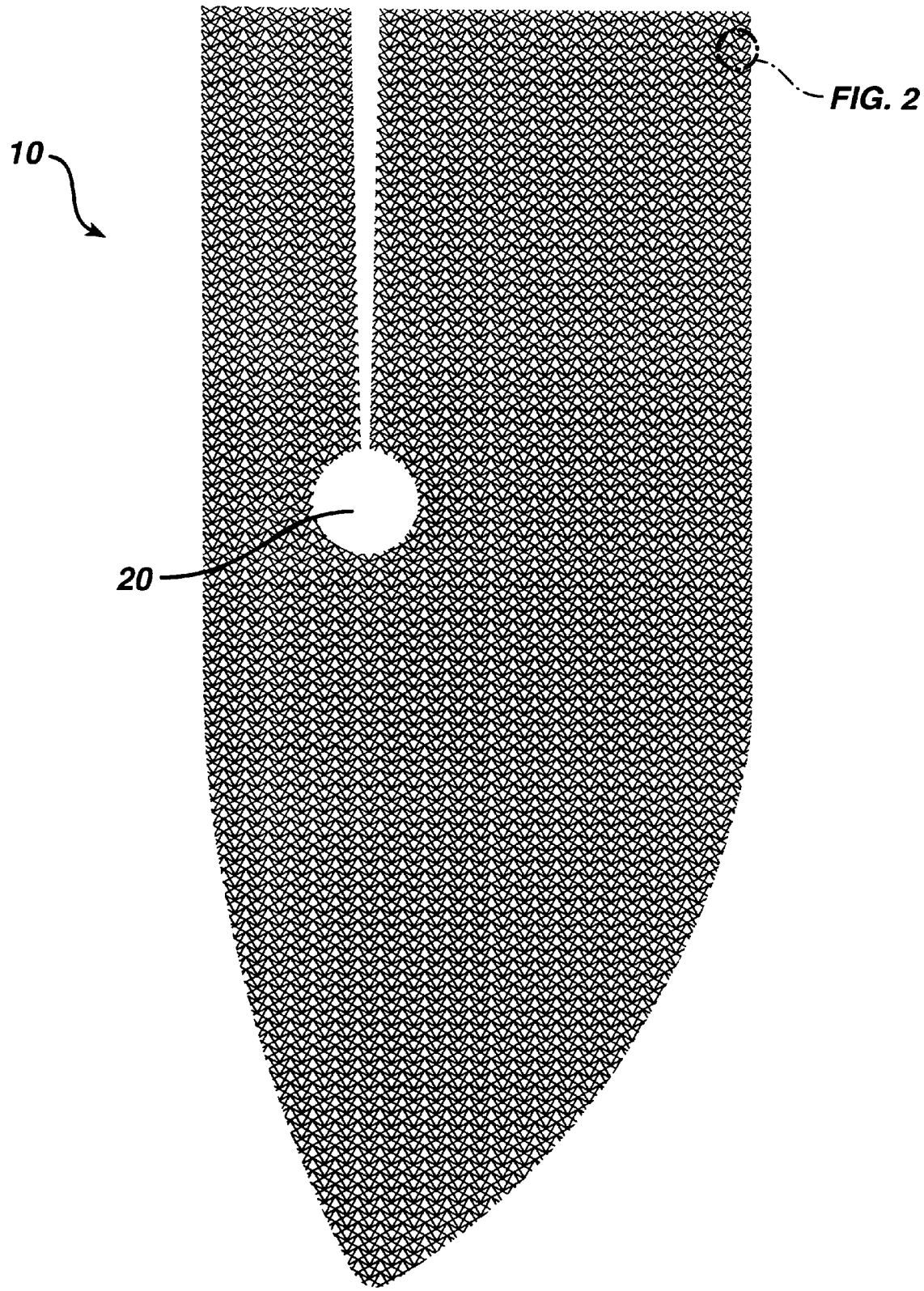
FIG. 1 illustrates a hernia repair patch 10 made with the inventive mesh having a key hole opening 20 forming a passage for the spermatic cord.
Figure 2:
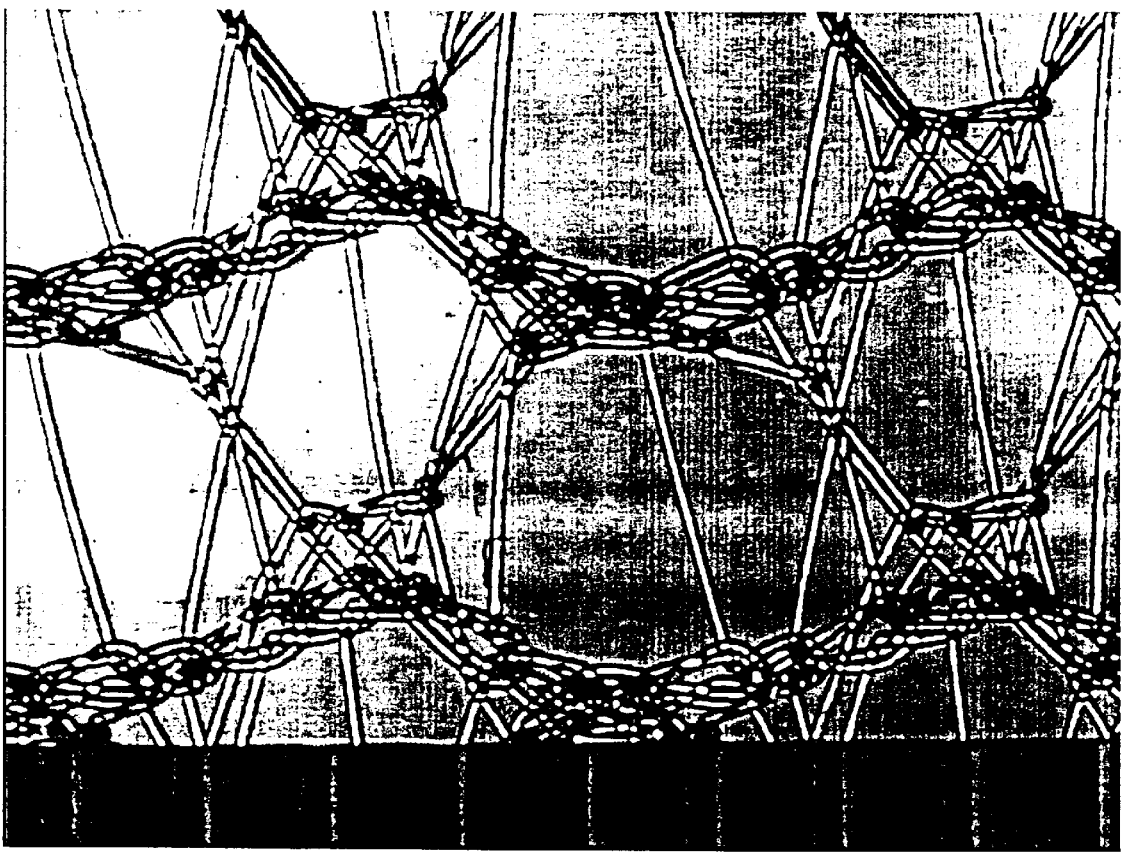
FIG. 2 is an enlarged view (photograph) of a portion of the surgical mesh shown in FIG. 1.

The surgical mesh of this invention is preferably fabricated from a yarn that is biocompatible. Preferred are yarns that have already been accepted for use as a suture material. Numerous biocompatible absorbable and non-absorbable yarns can be used to make the surgical meshes described hereinafter. Suitable non-absorbable materials for use in the present invention include, but are not limited to, cotton, linen, silk, polyamides (polyhexamethylene adipamide (nylon 66), polyhexamethylene sebacamide (nylon 610), polycapramide (nylon 6), polydodecanamide (nylon 12) and polyhexamethylene isophthalamide (nylon 61) copolymers and blends thereof), polyesters (e.g. polyethylene terephthalate, polybutyl terephthalate, copolymers and blends thereof), fluoropolymers (e.g. polytetrafluoroethylene and polyvinylidene fluoride) polyolefins (e.g. polypropylene including isotactic and syndiotactic polypropylene and blends thereof, as well as, blends composed predominately of isotactic or syndiotactic polypropylene blended with heterotactic polypropylene (such as are described in U.S. Pat. No. 4,557,264 issued Dec. 10, 1985 assigned to Ethicon, Inc. hereby incorporated by reference) and polyethylene (such as is described in U.S. Pat. No. 4,557,264 issued Dec. 10, 1985 assigned to Ethicon, Inc. hereby incorporated by reference)) and combinations thereof The preferred polypropylene yarns for the present invention utilizes as the raw material pellets of isotactic polypropylene homopolymer having a weight average molecular weight of from about 260,00 to about 420,000. Polypropylene of the desired grade is commercially available in both powder and pellet form.

Suitable absorbable materials for use as yarns include but are not limited to aliphatic polyesters which include but are not limited to homopolymers and copolymers of lactide (which includes lactic acid d-,l- and meso lactide), glycolide (including glycolic acid),ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one and polymer blends thereof.

Fibers and/or yarns may be made from absorbable and non-absorbable materials described above in heterologous yarns or bicomponent yarns. Additionally, fibers with different materials used in the sheath and core may also be used for the inventive surgical meshes.

In a preferred embodiment, the surgical mesh is fabricated from a monofilament yarn formed from a polypropylene resin, such as that disclosed in U.S. Pat. No. 4,911,165, entitled "Pliablized Polypropylene Surgical Filaments" and assigned to Ethicon, Inc., the contents of which is hereby incorporated in its entirety by reference. The preferred monofilament polypropylene yarn used has a diameter of from about 3.0 to about 6.0 mils, and more preferably a diameter of about 3.5 mils. Alternatively, a multifilament yarn, such as a multifilament polypropylene yarn may be used to fabricate a surgical mesh in accordance with the present invention.

Lubricants are commonly applied to these yarns before the yarns are knitted. Suitable lubricants can be either nontoxic hydrophobic lubricants such as waxes (i.e. low-melting hydrocarbons or esters of fatty acids alcohols or blends thereof such as Ethasew™ wax) or hydrophilic lubricants such as polyalkyl glycols i.e. polyethylene glycol with a molecular weight of from about 200 to 10,000 (as described in WO 98/37813 hereby incorporated by reference). The preferred lubricant is Ethasew™ wax which is a mixture of 50 percent sorbitan monopalmitate, 20 percent sorbitan tri-stearate and 30 percent sorbitan tri-stearate containing 20 mole percent ethylene oxide.

The surgical mesh of this invention is preferably fabricated from a 3.5 mil diameter monofilament polypropylene yarn by employing known and conventional warp knitting apparatus and techniques, such as the tricot and Raschel knitting machines and procedures described in "Warp Knitting Production" by Dr. S. Raz, Melliand Textilberichte GmbH, Rohrbacher Str. 76, D-6900 Heidelberg, Germany (1987), the contents of which are incorporated by reference herein. As expressly described therein, a course is a horizontal row of loops formed by the needles during one knitting cycle. In warp knitting, all the needles perform the knitting action simultaneously, so that one knitted course is formed across the whole width of the knitting machine for every turn of the main shaft. As is well known in the art of warp knitting, the number of courses and wales per inch in a knitted material is affected by a number of machine operating variables such as the rate at which the fabric is drawn away from the needles, the number of needles per inch, the amount of tension applied to the warp yarns and other variables after the fabric leaves the machine, e.g., the heat setting conditions. In the preferred embodiment of the present invention, the preferred polypropylene monofilament yarn described above is warp knitted, preferably tricot knitted on a 3 bar set-up, in accordance with the parameters set forth in Table I below:

TABLE I

| Courses per Inch | Wales per Inch | Back Bar | Middle Bar | Front Bar |
|---|---|---|---|---|
| 40–80 | 7–11 | 1–0 | 1–0 | 2–3 |
| | | 1–2 | 2–3 | 2–1 |
| | | 1–0 | 2–3 | 2–3 |
| | | 1–2 | 1–0 | 2–1 |
| | | 1–0 | 1–0 | 2–3 |
| | | 2–3 | 2–3 | 1–0 |
| | | 2–1 | 2–3 | 1–2 |
| | | 2–3 | 1–0 | 1–0 |

Figure 3:
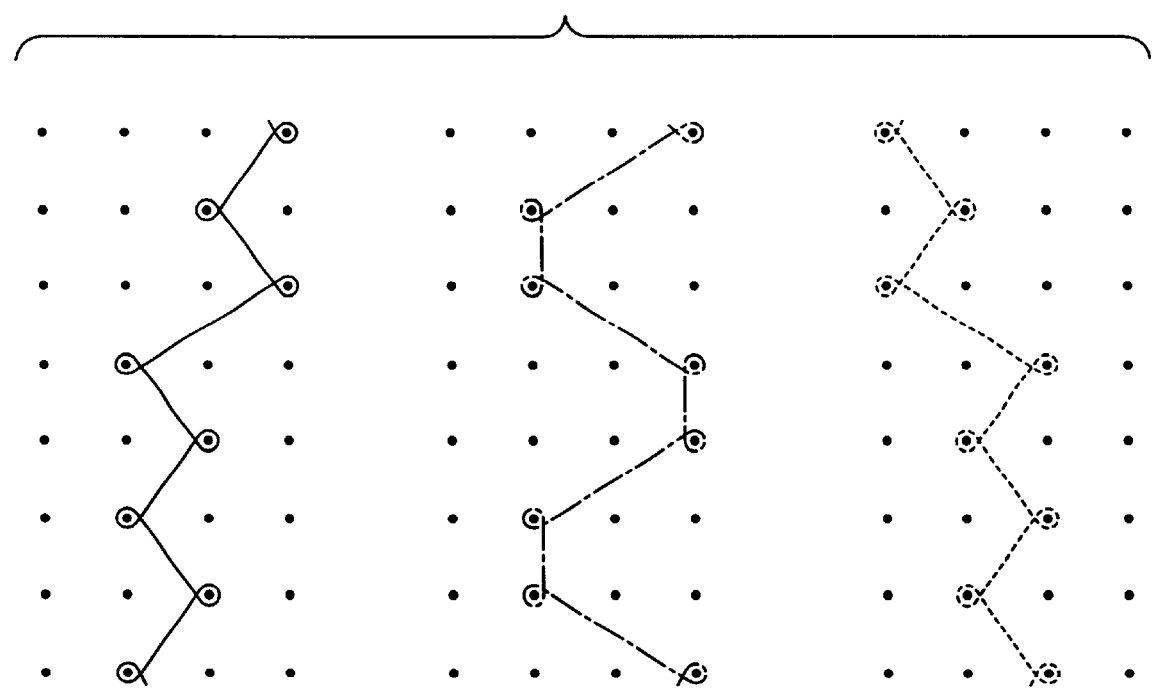
FIG. 3 is a diagram showing the pattern chain schematic for a knitted surgical mesh, in accordance with a preferred embodiment of the present invention.

Guide bar set-up threaded xoxo on all three bars. FIG. 3 illustrates a typical three bar set-up that may be used.

Following knitting, the mesh is cleaned or scoured, and thereafter annealed to stabilize the fabric. For the latter operation, the mesh can be secured to a tenter frame which maintains the mesh at a predetermined width, the frame then being passed through an elongated heating zone at a temperature of from about 100° C. to about 160° C., preferably at a temperature of from about 120° C. to about 150° C., at a rate providing a dwell time of from about 0.5 to about 60 minutes and preferably from about 1.5 to about 25 minutes. Following heat setting, the mesh is cut to size, packaged and sterilized.

The mesh can be cut to any desired configuration, e.g., a square or rectangular shape of appropriate dimensions. A preferred hernia repair patch 10 having a key-hole opening 20 is shown in FIG. 1. An ultrasonic slitter may be employed to cut the mesh, various types of which are commercially available. Unlike the result one obtains when cutting with a blade, i.e., frayed yarn ends, or when the yarn ends are heat-sealed, i.e., bead-like formations, cutting the mesh to size with an ultrasonic cutter avoids both frayed and beaded ends.

The polypropylene monofilament knitted mesh fabricated as described above exhibits good pliability. Depending on the yarn used to form the mesh, a mesh formed in accordance with Table I above preferably has a flexibility of about 100–250 mg-cm. In addition, depending on the yarn use to form the mesh, a mesh formed in accordance with Table I above preferably has a burst strength of about 100–190 pounds per square inch and, when the 3.5 mil diameter monofilament yarn described above is used, the mesh has a mean burst strength of 115 pounds per square inch which varies between about 105 to about 130 pounds per square inch depending on the sample. Finally, depending on the yarn used to form the mesh, a mesh formed in accordance with Table I above preferably has a pore size percentage greater than 50% and more preferably of from about 55% to about 70%, and, when the 3.5 mil diameter monofilament yarn described above is used the mesh has a pore size of about 65%. The polypropylene monofilament knitted mesh fabricated as described above preferably possesses a thickness of from about 16 to about 20 mils depending on the particular yarn used, and when the 3.5 mil diameter monofilament yarn described above is used, the mesh has a mean thickness of 17 mils which varies between about 17 to about 19 mils depending on the sample. The pore size percentage is the percentage of the area in the plane of the mesh not blocked by the fibers of the knitted mesh. The flexibility, burst strength and pore size characteristics for a mesh fabric, fabricated as described above and other meshes that are currently commercially available, are compared in Table II set forth below:

TABLE II

| Mesh Fabric | Average Flexibility (mg-cm/cm) | Burst Strength (PSI) | Weight (mg/cm$^2$) | Strength to Weight Ratio (lbs./mg) | Pore Size (%) | Thickness (Mils) |
|---|---|---|---|---|---|---|
| Present Invention | 190 | 115 | 4.61 | 3.87 | 65.5 | 17.5 |
| VISILEX ™ Mesh (mfd. by C. R. Bard) | 1228 | 148 | 7.1 | 3.23 | 52.7 | 29.5 |
| MERSILENE ™ Mesh (mfd. By Ethicon, Inc.) | 40 | 89 | 4.25 | 3.24 | 50.0 | 10.0 |
| MARLEX ™ Mesh (mfd. by C. R. Bard) | 786.3 | 186 | 10.95 | 2.63 | 41.3 | 25.9 |
| Surgipro ™ Mesh (mfd. by USSC,) | 1400 | 180 | 9.95 | 2.8 | 37.7 | 17 |

As shown in Table II the mesh of the present invention has: (i) a significantly better flexibility than the SURGIPRO™, VISILEX™ and MARLEX™ surgical mesh fabrics, and (ii) a significantly higher strength to weight ratio and (iii) a total porosity percentage greater than the SURGIPRO™, VISILEX™ and MARLEX™ mesh fabrics.

Furthermore, it is to be understood that although the present invention has been described with reference to a preferred embodiment, various modifications, known to those skilled in the art, may be made to the structures and process steps presented herein without departing from the invention as recited in the several claims appended hereto.

What is claimed is:

1. A knitted surgical mesh comprised of a knitted yarn, the knitted mesh having from about 40 to about 80 courses per inch and from about 7 to about 11 wales per inch three bar warp knit construction with a bar pattern set-up Front Bar: 2/3, 2/1, 2/3, 2/1, 2/3, 1/0, 1/2, 1/0: Middle Bar: 1/0, 2/3, 2/3, 1/0, 1/0, 2/3, 2/3, 1/0: Back Bar: 1/0, 1/2, 1/0, 1/2, 1/0, 2/3, 2/1, 2/3.

2. The knitted surgical mesh of claim 1, wherein the pore size percentage mesh is from about 55% to about 70%.

3. The knitted surgical mesh of claim 2, wherein the pore size percentage of the mesh is from about 62% to about 68%.

4. The knitted surgical mesh of claim 1, wherein the mesh has a burst strength from about 100 to about 140 pounds per square inch.

5. The knitted surgical mesh of claim 1, wherein the mesh has a thickness of from about 16 to about 20 mils.

6. The knitted surgical mesh of claim 5, wherein the thickness of the mesh is from about 17 to about 19 mils.

7. The surgical mesh of claim 1, wherein the yarn is a polypropylene yarn.

8. The surgical mesh of claim 7, wherein the yarn is a monofilament polypropylene yarn.

9. The surgical mesh of claim 8, wherein the yarn has a diameter of from about 3.0 to about 6.0.

10. The surgical mesh of claim 1, wherein the mesh includes a key-hole shaped opening within an interior region of the mesh.

11. The surgical mesh of claim 1, wherein the yarn is a multi-filament yarn.

12. The surgical mesh of claim 1, wherein the yarn is a monofilament yarn.

13. The surgical mesh of claim 1, wherein the yarn is a non-absorbable yarn made from a material selected from the group consisting of cotton, linen, silk, polyamides, polyesters, fluoropolymers, polyolefins and combinations thereof.

14. The surgical mesh of claim 1, wherein the yarn is an absorbable yarn made from a material selected from the group consisting of homopolymers and copolymers of lactide (which includes lactic acid d-, 1- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl- 1,4-dioxan-2-one and polymer blends thereof.

15. The surgical mesh of claim 11, wherein the yarn is made from polypropylene fiber.

16. The surgical mesh of claim 12, wherein the yarn is made from polypropylene fiber.

* * * * *